United States Patent
Tomita et al.

[11] Patent Number: 6,157,444
[45] Date of Patent: Dec. 5, 2000

[54] DEFECT INSPECTION APPARATUS FOR SILICON WAFER

[75] Inventors: Koji Tomita, Hitachinaka; Muneo Maeshima, Mito; Shigeru Matsui; Hitoshi Komuro, both of Hitachinaka; Kazuo Takeda, Tokorozawa, all of Japan

[73] Assignee: Hitachi, Ltd., Tokyo, Japan

[21] Appl. No.: 09/198,644

[22] Filed: Nov. 24, 1998

[30] Foreign Application Priority Data

Nov. 28, 1997 [JP] Japan ................................. 9-327570

[51] Int. Cl.$^7$ ................................................. G01N 21/88
[52] U.S. Cl. ...................................... 356/237.1; 356/446
[58] Field of Search ........................... 356/237.1, 237.2, 356/237.3, 446

[56] References Cited

U.S. PATENT DOCUMENTS 5,936,726  8/1999  Takeda et al. ........................ 236/237.2

OTHER PUBLICATIONS

A New Method for Measurement of Micro Defects near the Surface of Si Wafers –Optical Shallow Defect Analyzer (OSDA)–, Kazuo Takeda, et al., pp. 151–153—The Japan Society of Applied Physics.

Applied Physics vol. 65, No. 11(1996) pp. 1162 to 1163.

*Primary Examiner*—Richard A. Rosenberger
*Attorney, Agent, or Firm*—Kenyon & Kenyon

[57] ABSTRACT

In order to easily evaluate defects of the silicon wafer affecting the characteristic of a device, the present invention provides a defect inspection apparatus for detecting defects existing on a surface of a sample and/or inside the sample, which comprises a display apparatus for displaying a distribution of the defects on a graph having coordinate axes of distance from a central position of the sample and the depth where the defect exists based on the depth information and the positional information obtained by a detecting means.

3 Claims, 9 Drawing Sheets

DEFECT INSPECTION APPARATUS FOR SILICON WAFER

BACKGROUND OF THE INVENTION

The present invention relates to an inspection apparatus for a semiconductor defect and particularly to an inspection apparatus for a defect such as a precipitated particle or a stacking fault in a silicon wafer.

As the integration of a LSI (large scale integrated circuit) is being increased, decrease in a conforming item acquisition ratio and decrease in reliability caused by a failed MOS (metal oxide semiconductor) transistor composing the LSI becomes a large problem. As causes of the failed MOS transistor, dielectric breakdown of a gate oxide film and excessive leak current in a junction are typical problems. It is not preferable that a crystal defect is formed in a surface area having elements on a silicon wafer because a failed MOS transistor occurs, as described above.

Therefore, defect measurement is important in the quality control of silicon crystal. In regard to the method measuring such a defect, there is a method in which an infrared ray transmissible through the silicon is irradiated and the scattered light is detected. In such a measuring method, it is necessary to measure defect sizes and defect positions in the depth direction. This is because an effect of defect on the device differs depending on the defect size and the defect position in the depth direction. A technology to observe crystal defects is described in "Extended Abstracts of the 1996 International Conference on Solid State Devices and Materials, pages 151–153" and "Applied Physics, Vol. 65, No. 11 (1996)", pages 1162–1163.

In this technology, a light beam composed of two wavelengths of which absorptivities are different from each other by one digit is irradiated onto a wafer surface, and intensity of the scattered light from a defect is measured for each of the wavelengths to obtain a position of the defect in the depth direction and a dimension of the defect. The paper discloses a planar distribution diagram of defects inside a wafer detected by the technology, a display having depth from the surface in the abscissa and number of defects in the ordinate, and a distribution diagram having distance toward the radial direction from the center of a wafer in the abscissa and defect size in the ordinate. Defect inspection is performed to obtain the distribution diagrams and the displays described above, and to specify the distribution of defects existing on the surface of a wafer and inside the wafer and the trend of the defect production. It is well known that when very small stacking faults among the crystal defects are produced in an active region of a device, the characteristic of the device is hurt such as by increasing of the leak current.

Further, it is reported that the withstanding voltage characteristic of an initial oxide film strongly depends on a crystal pulling-up speed at crystal growth. This shows that a grown-in defect existing in the crystal just after crystal growth affects the electric characteristic.

SUMARRY OF THE INVENTION

As described above, when the crystal defect is evaluated from the viewpoint of effect on a device, a technology capable of quantitatively evaluating very small (smaller than several nm) and low density (lower than $10^5/cm^3$) defects is required.

Further, it is also important for the wafer manufacturing process to identify which process in the semiconductor wafer manufacturing process a defect is produced in, for example, to identify that the defect is a defect caused by working such as surface polishing, a grown-in defect at crystal pulling-up or a defect in crystal induced in a process such as heat treatment.

The method of displaying a wafer planar distribution of defects can qualitatively express the distribution, uniform or non-uniform, but has a disadvantage as that the distribution density cannot be quantitatively expressed.

The method of displaying number of defects on the depth basis using histogram has a disadvantage in that the value of the number of defects on the depth basis cannot be used as an absolute value because the detectable depth varies depending on defect size.

The method of displaying a scatter diagram of distance toward radial direction from a center and defect size can express a general trend of distribution, but has a disadvantage in that judgment on whether or not distribution of defects is increased toward the peripheral direction largely depends on an experiment of an evaluating person and accordingly it is difficult that everyone has the same judgment.

An object of the present invention is to provide a defect inspection apparatus, which can quantitatively evaluate defects affecting the characteristic of a device, and can commonly and easily specify defect cause on a working process.

In order to solve the above-mentioned problems, firstly the present invention provides a defect inspection apparatus for detecting defects existing on a surface of a sample such as silicon wafer etc. and/or inside the sample based on light information from the sample obtained by irradiating a light beam onto the sample, which comprises a detecting means for detecting a depth where the defect exists and a position of the defect based on the light information; and a display apparatus for displaying a distribution of the defects on a graph having coordinate axes of distance from a central position of the sample and the depth where the defect exists based on the depth information and the positional information obtained by the detecting means.

Secondarily, the present invention provides a defect inspection apparatus for detecting defects existing on a surface of a sample and/or inside the sample based on light information from the sample obtained by irradiating a light beam onto the sample, which comprises a detecting means for detecting a size of the defect and a position where the defect exists based on the light information; and a display apparatus for displaying an average defect size at each corresponding distance from a central position of the sample on a graph having coordinate axes of the distance from the central position of the sample and the size of said defect based on the size information and the positional information obtained by the detecting means.

Thirdly, the present invention provides a defect inspection apparatus for detecting defects existing on a surface of a sample and/or inside the sample based on light information from the sample obtained by irradiating a light beam onto the sample, which comprises a detecting means for detecting a position of the defect based on the light information; and a display apparatus for displaying a defect density per unit area and/or per unit volume for each corresponding distance from a central position of the sample on a graph having coordinate axes of distance from the central position of the sample and the defect density per unit area and/or unit volume based on the positional information obtained by the detecting means.

Fourthly, the present invention provides a defect inspection apparatus for detecting defects existing on a surface of a sample and/or inside the sample based on light information from the sample obtained by irradiating a light beam onto the sample, which comprises a detecting means for detecting a position of the defect and an intensity of the light information based on the light information; and a display apparatus for displaying a distribution of the defects on a graph having coordinate axes of angle relative to a center of the sample and intensity of light information based on the positional information and the intensity information obtained by the detecting means.

Fifthly, the present invention provides a sample surface observing apparatus for detecting scattered light from a sample obtained by irradiating light onto the sample, which comprises a detected frequency for each intensity of the scattered light on a graph having coordinate axes of intensity of the scattered light and detected frequency of the intensity of scattered light.

Sixthly, the present invention provides a defect inspection apparatus for detecting defects existing on a surface of a sample and/or inside the sample based on light information from the sample obtained by irradiating a light beam onto the sample, which comprises a means for detecting a haze of the sample based on the light information; a means for detecting a position of the defect based on the light information; and a display apparatus for displaying a distribution of the hazes by superposing on a distribution of the defects based on said detected haze and the defect position information.

Seventhly, the present invention provides a defect inspection apparatus for detecting defects existing on a surface of a sample and/or inside the sample based on light information from the sample obtained by irradiating a light beam onto the sample, which comprises a detecting means for detecting a depth where the defect exists and a size of the defect based on the light information; and a display apparatus for displaying a distribution of the defects on a graph having coordinate axes of depth of the defect and size of the defect based on the depth information and the size information obtained by the detecting means.

DETAILED DESCRIPTION OF THE PREFERRED EMBODIMENTS

An apparatus of the present embodiment is composed of at least two light sources emitting light beams which are absorbed in a sample and have wavelengths different from each other in penetrable depth by three times or more, or a light source emitting a light beam of at least double-wavelength similar to the above at a time; a means for irradiating each of the light beams onto the sample; a means for scanning the irradiating light beam to the sample, or a means for scanning the sample to the irradiating light beam; a means for monitoring the scanning position; a detecting system which separates scattered light produced by a defect on the sample surface or inside the sample into each of light beams having the irradiating wavelengths, respectively condensing the separated light beams, detecting the condensed light beams using light detectors respectively by each wavelength; an electric system which sets a threshold value to a scattered light intensity signal of one specified wavelength between the two wavelengths to form a trigger signal, and a scattered light intensity and a defect detected position of the other wavelength are digitized and acquired in a memory only when a signal of the one specified wavelength larger than the threshold value is detected; a data processing system for calculating a defect size from a scattered light signal of the wavelength having a longer penetrable depth; a data processing system for deriving a position Z of a defect in the depth direction using the scattered light intensities of the two wavelengths; and a display system for displaying a depth distribution by distance in the radial direction from the center, an average defect size distribution by distance in the radial direction from the center, a defect density distribution by distance in the radial direction from the center, a line graph of average defect size superposed on a defect size distribution by distance in the radial direction from the center, a defect size distribution by angle from the center, a frequency distribution by haze intensity, and a distribution of defect measured result superposed on a planar distribution of haze intensity.

Figure 4:
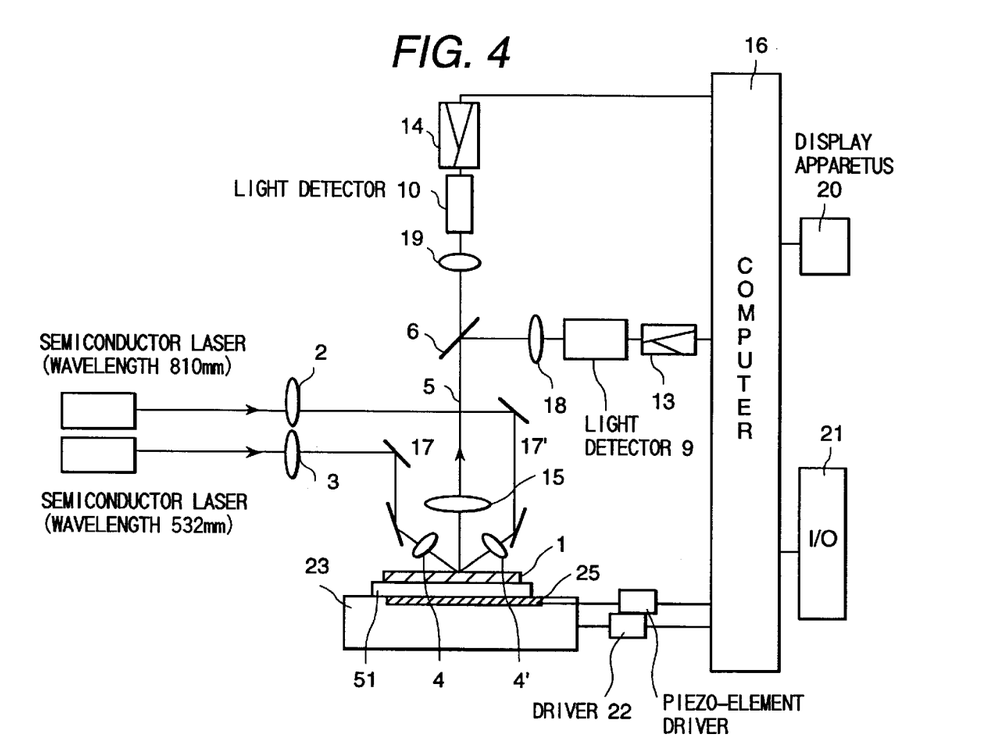
FIG. 4 is a schematic view showing an embodiment of a defect inspection apparatus in accordance with the present invention.

The apparatus of the present embodiment composed of the above-mentioned components will be further described, referring to FIG. 4.

A sample is a silicon wafer. A laser beam having a wavelength of 810 nm from a semiconductor laser and a second harmonic laser beam (SHG) having a wavelength of 532 nm from a YAG laser are respectively paralleled by lenses 2 and 3 in p-polarization direction to the surface of the sample wafer 1, and concentrated by mirrors 17 and 17' and lenses 4 and 4', and then irradiated onto the surface of the silicon wafer 1.

In this occasion, the measurement is performed by displacing the irradiating position of the light beam of 532 nm wavelength by a distance of about several times of the irradiating beam diameters (approximately 5 μm) so that the light beam of 532 nm wavelength is irradiated earlier than the light beam of 810 nm wavelength in time as the light beams are scanned. Detection of a defect is set so that the both signals of 532 nm wavelength and 810 nm wavelength are acquired only when a scattered light intensity signal (S2) of 532 nm wavelength exceeds a preset threshold value. Therein, the threshold value is set so that a scattered light intensity fluctuation generated from the wafer surface is not detected as a signal.

As the irradiating region is scanned on the wafer surface, a crystal defect such as an oxygen precipitation particle ($SiO_2$ particle), a transition or the like contained the sample wafer is detected by detecting scattered light generated from the defect inside the wafer at a moment when the irradiation region passes through the defect. The scattered light 5 from the defect is concentrated using a lens 15, and separated to a light beam of 810 nm wavelength and a light beam of 532 nm wavelength by a dichroic mirror 6, and respectively concentrated by lenses 18 and 19, then respectively detected using light detectors 9 and 10. The detected signals are respectively amplified by amplifiers 13 and 14, and digitized by A/D converters to be acquired in a computer 16.

On the other hand, scattered light measurement is performed while the rotating stage 23 is scanned in a rotating direction (θ direction) and a radial direction (R direction) using a driver 22 by the computer 16 and while coordinates (R, θ) of a rotation encoder and a linear encoder attached to the wafer fixing jig 51 are being monitored. Display modes specific of the present embodiment to be described later is displayed by a display apparatus 20.

Fluctuation of the height of the wafer surface during measuring is controlled within a focal depth of the objective lens 15 by providing a gap sensor (not shown) near the objective lens 15 and using a servo mechanism utilizing a piezo-element 25.

The principle for obtaining a position of a defect in the depth direction and a particle size of a defect will be described below. The computer 16 of FIG. 4 in this embodiment has a function to execute the following calculations.

Letting a refractive index of a sample substance for wavelength λ be n and an attenuation coefficient be k, the penetrable depth Γ where an amplitude of the incident light becomes 1/e of a value just below the surface of the substance can be expressed by the following equation 1.

$$\Gamma = \lambda/2\pi k \quad (1)$$

Therefore, by considering that the refractive index of silicon is arc sine(sin θ/n), an intensity at a depth Z from the surface of light incident to the substance from air atmosphere with an incident angle θ is attenuated from the intensity at just below the surface by $\exp((-2Z/\Gamma)\cos(\arcsin(\sin\theta/n)))$.

Supposing that the light beam is irradiated from air atmosphere onto the sample surface at an incident angle θ, the irradiated light beam is scattered by a defect inside the sample toward the direction of the sample surface, and the scattered light is detected with a certain solid angle. With considering both of attenuation of the irradiated light beam and attenuation of the scattered light, an intensity S of scattered light from the defect which exists at a position of a depth Z from the surface of the substance can be expressed by the following equation 2. Therein, σ is an integrated scattering cross section in respect of the certain solid angle, I is an intensity of the incident light beam, Ti is a transmissivity of the incident light beam at an incident angle on the surface, and Ts is a transmissivity of the scattered light of the defect to the air atmosphere from the inside of the wafer.

$$S = Ti \cdot Ts \cdot I \cdot \sigma \cdot \exp[-(2Z/\Gamma)(1+1/\{\cos(\arcsin(\sin\theta/n))\})] \quad (2)$$

Letting refractive indexes of a substance for wavelengths $\lambda 1, \lambda 2$ be $n1, n2$, penetrable depths be $\Gamma 1, \Gamma 2$, intensities of incident light beams be $I1, I2$, intensities of measured scattered light be $S1, S2$, integrated scattering cross sections be $\sigma 1, \sigma 2$, transmissivities of the irradiated light beams be $Ti1, Ti2$, and transmissivities of the scattered light be $TS1, TS2$, respectively, the following equations 3 and 4 are satisfied.

$$S1 = Ti1 \cdot TS1 \cdot I1 \cdot \sigma 1 \cdot \exp[-(2Z/\Gamma 1)(1+1/\{\cos(\arcsin(\sin\theta/n1))\})] \quad (3)$$

$$S2 = Ti2 \cdot TS2 \cdot I2 \cdot \sigma 2 \cdot \exp[-(2Z/\Gamma 2)(1+1/\{\cos(\arcsin(\sin\theta/n2))\})] \quad (4)$$

Therein, it is assumed that $\Gamma 1 > \Gamma 2$. From the equation 3 and the equation 4, the following equation 5 can be obtained.

$$Z = C1 \cdot \ln[C2(S1/S2)(\sigma 2/\sigma 1)] \quad (5)$$

where C1 and C2 are determined by constants of the apparatus and optical constants of the sample, and are defined by the following equations 6 and 7.

$$C1 = 1/[(2/\Gamma 2)(1+1/\{\cos(\arcsin(\sin\theta/n2))\}) - (2/\Gamma 1)(1+1/\{\cos(\arcsin(\sin\theta/n1))\})] \quad (6)$$

$$C2 = (I2/I1) \cdot (T2i\ TS2/T1i\ TS1) \quad (7)$$

Since C1 and C2 are constants of the apparatus, Z can be calculated if $(S1/S2)(\sigma 2/\sigma 1)$ is known.

The ratio $(S1/S2)$ is a ratio of signal intensities and can be obtained from measured values. A method of obtaining the ratio $(\sigma 2/\sigma 1)$ will be described below.

Since the values σ1 and σ2 can be calculated from defect particle size using conventional Mie's scattering theory and conventional scattering theory in an absorptive medium, the principle of particle size measurement will be described below. A signal intensity S1 of a defect existing within a penetrable depth Γ2 detected by a signal intensity S2 is considered. When the condition $\Gamma 1 \gg \Gamma 2$ is satisfied, the attenuation factor of the S1 becomes 1 and accordingly the attenuation is negligible. This is because the position Z of the defect in the depth direction satisfies the relation Z<Γ2. This relation will be quantitatively described below.

In order to measure the defect size, for instance, within 10%, an allowable attenuation of the signal intensity S1 by depth will be considered. In most of actual measurement, since particle sizes of defects is below 0.1 μm, the scattering can be regarded as Rayleigh scattering in which an scattered light intensity by a defect is in proportion to the sixth power of the particle size and in proportion to the minus fourth power of the wavelength.

Figure 1:
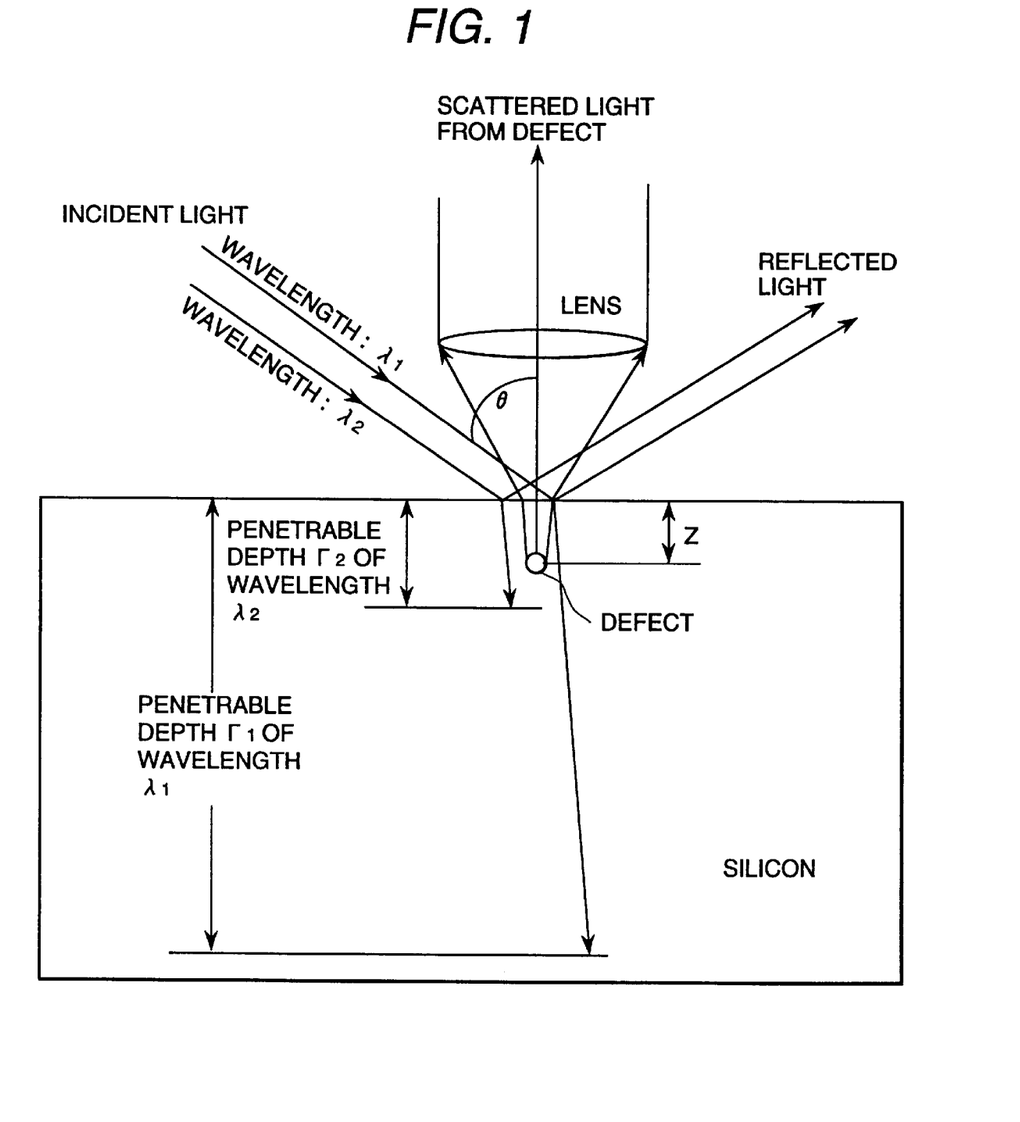
FIG. 1 is a view explaining an embodiment of a measuring method in accordance with the present invention.
Figure 2:
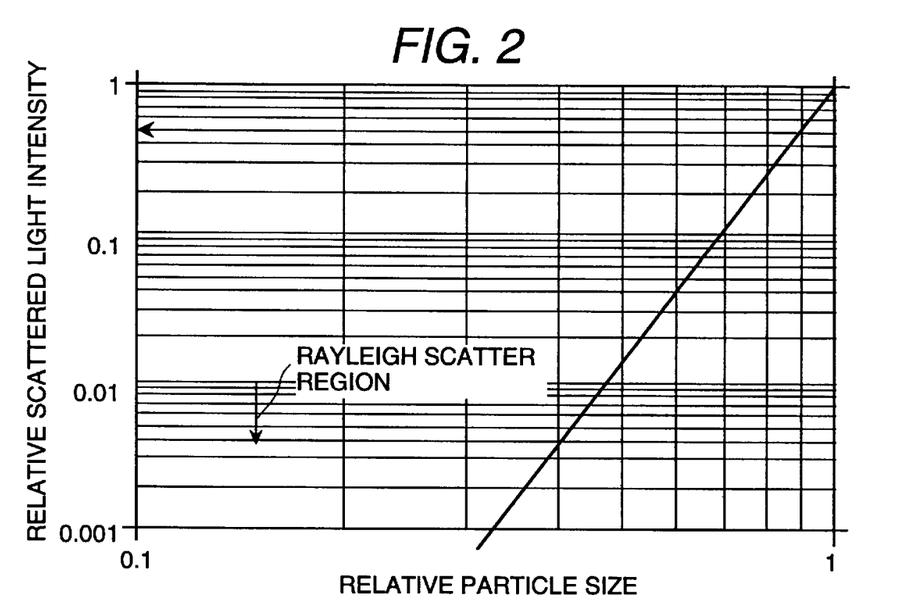
FIG. 2 is a graph explaining the relationship between particle size measuring accuracy and scattered light measuring accuracy.

FIG. 2 shows the relationship between relative particle size and relative scattered light intensity when the particle size is sufficiently smaller than the wavelength and within the Rayleigh scatter region shown in the figure. It can be understood that the relative scattered light intensity necessary to be 50% in order to bring the relative particle size within 10%.

Figure 3:
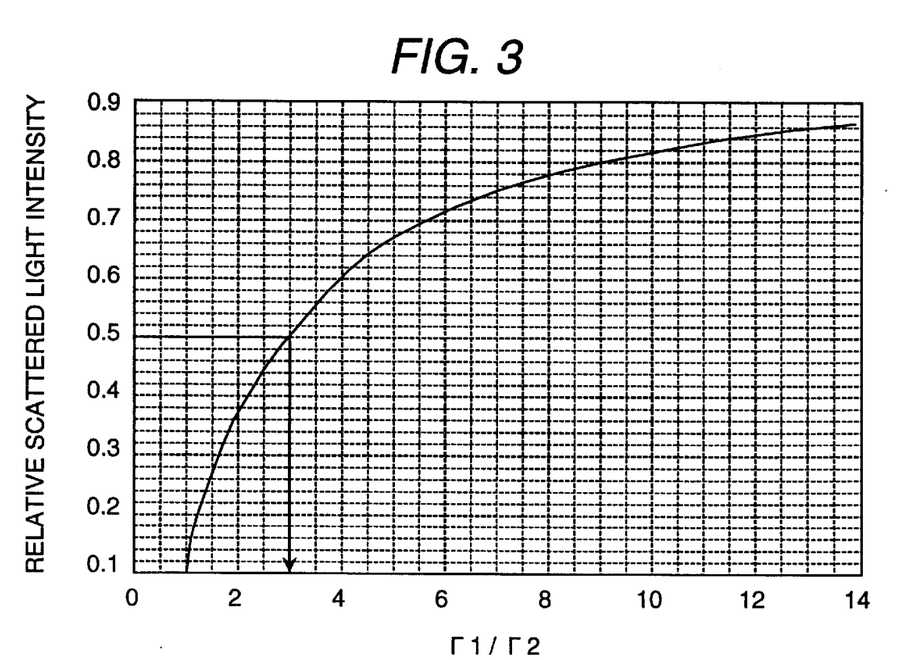
FIG. 3 is a graph showing attenuating rate of scattered light intensity depending on the depth for determining a ratio of penetration depths of two wavelengths and a particle size.

In regard to the defect signal S1 detected within Γ2, the relationship of FIG. 3 can be obtained by substituting the relation Z=Γ2 into Equation 3 as the condition that the attenuation ratio by depth is smaller than 50%. From the relationship, the condition of Γ1/Γ2>3 can be obtained. In a case of employing a combination of 532 nm wavelength and 810 nm wavelength, the ratio of the penetrable depths is approximately 10, and accordingly the above condition is satisfied. Further, the value ($\sigma 2/\sigma 1$) does not depend on the defect size in Rayleigh scattering, but depends only on the irradiated wavelengths as shown by the following equation 8.

$$(\sigma 2/\sigma 1)=(\lambda 1/\lambda 2)4 \quad (8)$$

By substituting the above equation into Equation 5, the depth measurement equation 9 is simplified as follows.

$$Z=C1 \ln(S1/S2)+C0 \quad (9)$$

where C0 is a constant of the apparatus as shown by the following equation 10.

$$C0=C1 \ln[C2(\lambda 1/\lambda 2)4] \quad (10)$$

A particle size d can be expressed as a following equation 11, since S1 is in proportion to the sixth power of d.

$$\ln(d)=(1/6)\ln(S1)+C3 \quad (11)$$

where C3 is a constant of the apparatus which is a function of detection angle and irradiation intensity. The constants of the apparatus such as C0 and C1 may be determined by measuring a reference sample. In this case, suitable reference particles for particle size are polystyrene particles having a known particle size attached onto a wafer surface, and a suitable reference sample for depth is an epitaxial wafer having an epitaxial layer of a known thickness. The reason why an epitaxial wafer is used as the reference sample for depth is that the epitaxial wafer can be used as a reference sample for distribution of defect density in the depth direction since defect density in the epitaxial layer is very small compared to defect density inside a substrate under the epitaxial layer.

The apparatus of this embodiment comprises a function to integrating the information such as depths or particle sizes calculated by the above-described equations by a predetermined unit such as predetermined depth or predetermined particle size and to count them by each unit. This counting is performed by the computer 16. Further, the apparatus comprises a function to calculate defect information according to display modes specific to the embodiment which is to be described later.

Figure 5:
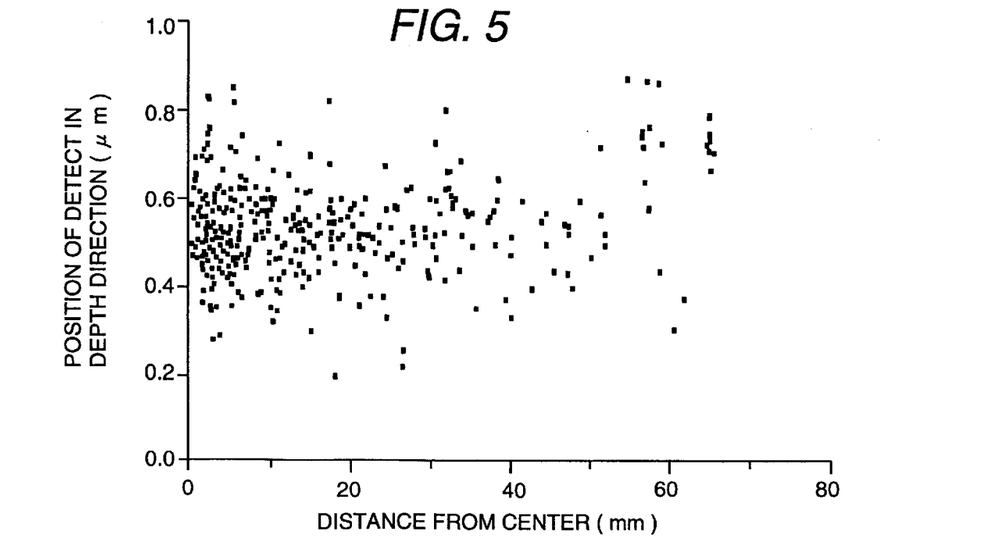
FIG. 5 is a graph showing an example of a display of defects in a silicon wafer expressed by distribution in the depth direction at each position of radial distance from the center.

FIG. 5 is a graph showing a display of a measured result of defects in the silicon wafer expressed by distribution in the depth direction at each position of radial distance from the center.

The axis expressing the depth can be expressed by equation 9. By specifying the position of detected wafer defects using a position in the radial direction and a position in the depth direction, it is possible to verify, for example, the thickness of the epitaxial layer in the epitaxial wafer. Since the defect density inside the epitaxial layer is lower than the defect density inside the substrate under the epitaxial layer by one to two digits, the thickness of the epitaxial layer can be judged by observing the distribution of defects in the depth direction. Further, it is possible to easily identify cause of defects from defects intensively distributed in the interface between the epitaxial layer and the substrate, for example, whether the defects are defects caused by working such as polishing or defects depending on crystal growth such as grown-in defects.

For example, in a hydrogen annealing of the wafer, the shallower the position of the defects are and the smaller the size of the defects are, the more defects disappears, and there is a general tendency in the grown-in defects of a CZ wafer as that the size of the grown-in defects are larger in the central part of the wafer and smaller in the peripheral part of the wafer.

Therefore, a depth profile of the defects in the case of the annealing of the CZ wafer, the defects of the shallow region remain in the central part of the wafer and the defects up to the deep region disappears in the peripheral part of the wafer, and the depth distribution of the defects are varied according to a distance from the center of the wafer. Referring to these facts, a progress degree of the hydrogen annealing of the wafer is capable to be measured by displaying this profile.

Figure 6:
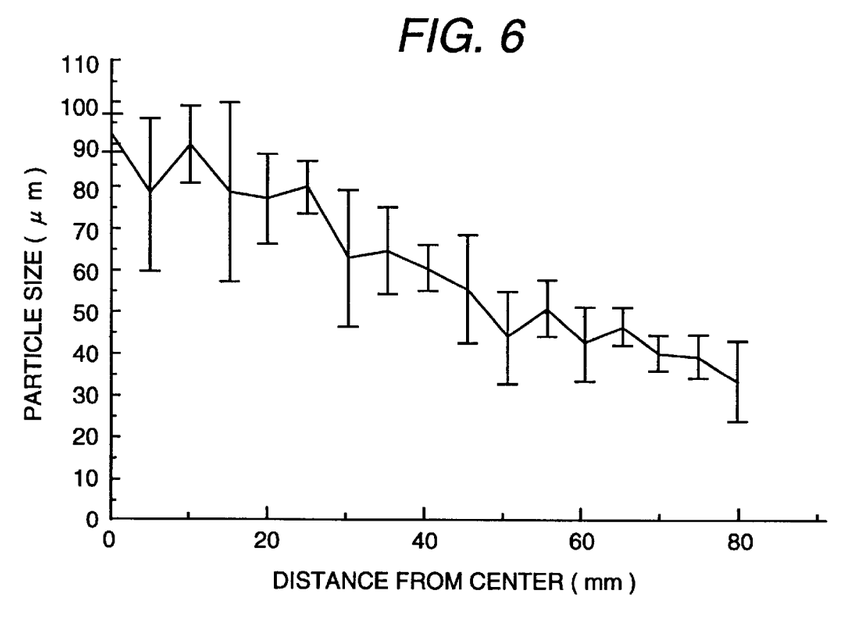
FIG. 6 is a graph showing an example of a display of defects in a silicon wafer expressed by a line of average defect particle size at each position of radial distance from the center.

FIG. 6 is a graph showing a display of measured results of defects in a silicon wafer expressed by a line of average defect particle size by radial distance from the center (by each preset distance). The axis expressing defect size can be expressed by a scale in proportion to size if a value in proportion to S1 is taken by the equation 11.

The scale of the axis may be graduated a peak position of a particle size distribution obtained by measuring a wafer having polystyrene particles of a known particle size on the wafer surface as a particle size on the basis of known polystyrene particle size. An average value of defect sizes and a standard deviation for each certain radial distance (preset distance unit), and the defect size is expressed by line and the line segment of standard deviation in each point is displayed vertically on the average value point. By doing so, the peak position and the half value width of the size distribution for each position in the radial direction can be clearly expressed as numerical values. Since the size distribution from the inner peripheral portion of the wafer to the outer peripheral portion can be objectively identified by the line graph of quantitative values, it is possible to easily identify cause of defects whether the defects are defects caused by working such as polishing or defects depending on crystal growth such as grown-in defects.

Further, the quantification enables to perform feedback to the other process or the like based on the numerical values.

In a distribution graph having distance from a center in the abscissa and particle size in the ordinate illustrated in the 1996 International Conference on Solid State Devices and Materials, pages 151–153, there is a problem in that it is difficult to judge a steep change in the particle size to the distance from the center.

For example, there is a process to manufacturing a single crystal ingot of a raw material of silicon wafers in a silicone wafer manufacturing processes. In a manufacturing method called as CZ method among them, high purity silicon is melted in a high purity quartz crucible together with a dopant, and a seed crystal is dipped into the molten silicon and then pulled up at a slow speed while being rotated to manufacture a single crystal.

At that time, defects called as OSF ring are sometimes produced depending on the pulling condition or the temperature condition. In general, the particle size of defects gradually becomes small toward the outer peripheral direction of a wafer, as shown in FIG. 6. However, when the OSF ring exists, the particle size distribution rapidly changes at a certain position. Such a change can be exactly captured by the line graph display as shown in FIG. 6. Further, by the display, it is possible to easily perform feedback to setting of the pulling-up condition of ingot and the temperature condition.

Figure 7:
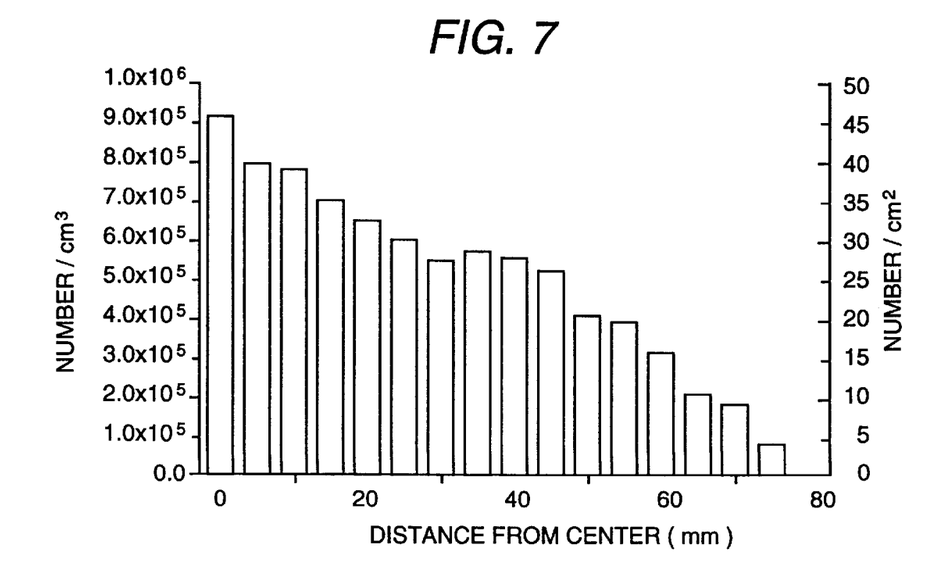
FIG. 7 is a graph showing an example of a display of defects in a silicon wafer expressed by distribution of defect density at each position of radial distance from the center.

FIG. 7 is a graph showing a display of a measured result of defects in a silicon wafer expressed by distribution of defect density at each position of radial distance from the center. The axis expressing the density can be displayed number of defects per unit volume or number of defects per unit area from detectable depth of the defects.

Referring that the profile shown in FIG. 5 gives an impression as that the defect density in the peripheral part looks like to be larger than an actual one, the embodiment shown in FIG. 7 is proposed to show the defect density correctly.

Therefore, by referring to the defect density shown in FIG. 7 in comparison with the profile shown in FIG. 5, it becomes possible to correctly judge the grown-in defect, and because the grown-in defect is changed according to not only the size but the defect density, the most suitable condition to pull up a silicon ingot so as to make the grown-in defect minimum is easily obtained.

Since the display shows what position in the radial direction of the wafer many defects exist in and accordingly it is possible to objectively judge whether distribution of the defects is uniform or not, it is possible to easily identify cause of defects whether the defects are defects caused by working such as polishing or defects depending on crystal growth such as grown-in defects. Further, the quantification enables to perform feedback to the other process or the like based on the numerical values.

As described above, the single crystal ingot is pulled up from the crucible while being rotated. In this rotating pulling-up process, the same atoms as the atoms of the seed crystal are arrayed to form the single crystal ingot. That is, the graph having the coordinate axis of distance form the center is extremely effective to specify a problem in the pulling-up process.

However, if the above-mentioned trend is tried to be specified using the graph having the coordinate axes of distance from the center and number of defects, there is the following problem.

That is, since the observed area per unit length in the radial direction increases toward the peripheral portion of the wafer, the increasing and decreasing trend of number of defects cannot be appropriately judged.

The present embodiment solves such a problem, and provide a defect inspection apparatus which perform a display suitable for appropriately judging the increasing and decreasing trend of number of defects.

Figure 8:
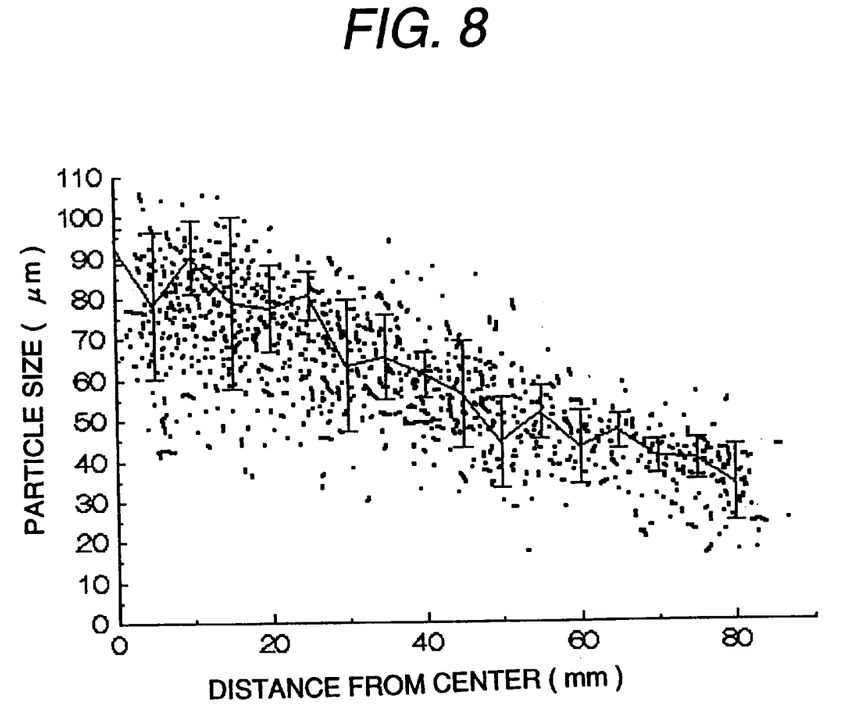
FIG. 8 is a graph showing an example of a display of defects in a silicon wafer expressed by superposing the distribution of defect particle sizes on the line of average defect particle size at each position of radial distance from the center.

FIG. 8 is a display of a measured result of defects in a silicon wafer expressed by superposing the distribution of defect particle sizes on the line of average defect particle size at each position of radial distance from the center. By superposing a scatter diagram showing a spreading feature of the distribution, two kinds of information can be displayed on one plot area, and accordingly the size distribution and the trend from the inner peripheral portion of the wafer to the outer peripheral portion can be identified clearer. By this display, it is possible to easily identify cause of defects whether the defects are defects caused by working such as polishing or defects depending on crystal growth such as grown-in defects. Further, in addition to the distribution trend, the quantification enables to perform feedback to the other process or the like based on the numerical values.

Figure 9:
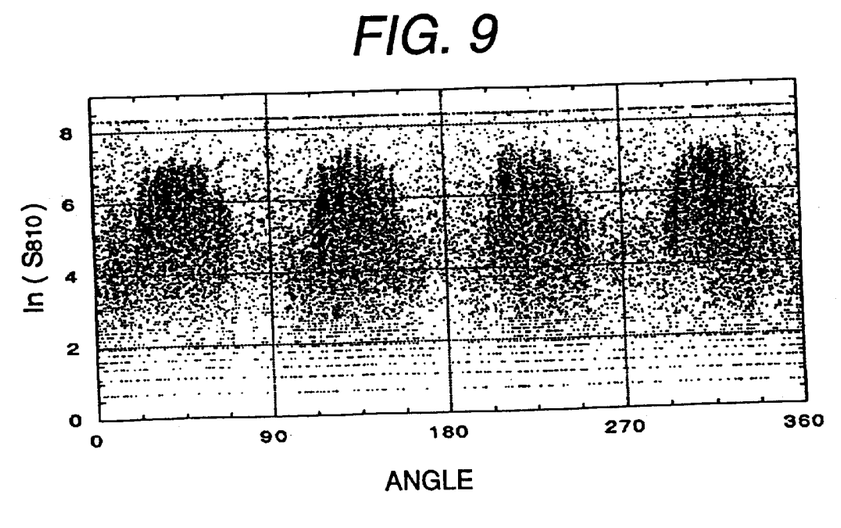
FIG. 9 is a graph showing an example of a display of defects in a silicon wafer expressed by overlapping the distribution of defect particle sizes from the center in each angle.

FIG. 9 is a display of a measured result of defects in a silicon wafer expressed by overlapping the distribution of defect particle sizes from the center in each angle. The axis expressing defect sizes can be expressed by graduation in proportion to defect size by taking a value in proportion to $S1.(1/6)$. By these plots, it is possible to check anisotropy expressing that the shape of defects is not spherical. That is, in a case of Rayleigh scattering, the differential scattering cross section is unnecessary to take the effect of the shape, sphere or non-sphere, into consideration. However, in a case of Mie scattering, the differential scattering cross section is affected by the shape. In a case of nearly spherical shape defects (for example, octahedron) or in a case of defects in Rayleigh scattering region, the angle dependence becomes uniform.

If the angle dependence occurs as shown in FIG. 9, it can be understood that the shape of the defects is non-spherical (for example, plate-shaped oxygen precipitation particles) or the defects have a size in Mie scattering region (large size). As described above, since the defect shapes can be specified, it is possible to specify detailed contents of defects such as oxygen precipitating particles, vacant lattice points among defects depending on the crystal growth process, and it is also possible to easily perform appropriate feedback to the working process. Further, since observation is performed while the stage mounting the sample is being rotated in the apparatus of this embodiment, different distributions are sometimes displayed depending on shape of the defects, arrangement or light irradiation direction. Therefore, this display capable of checking such trends is effective.

Figure 10:
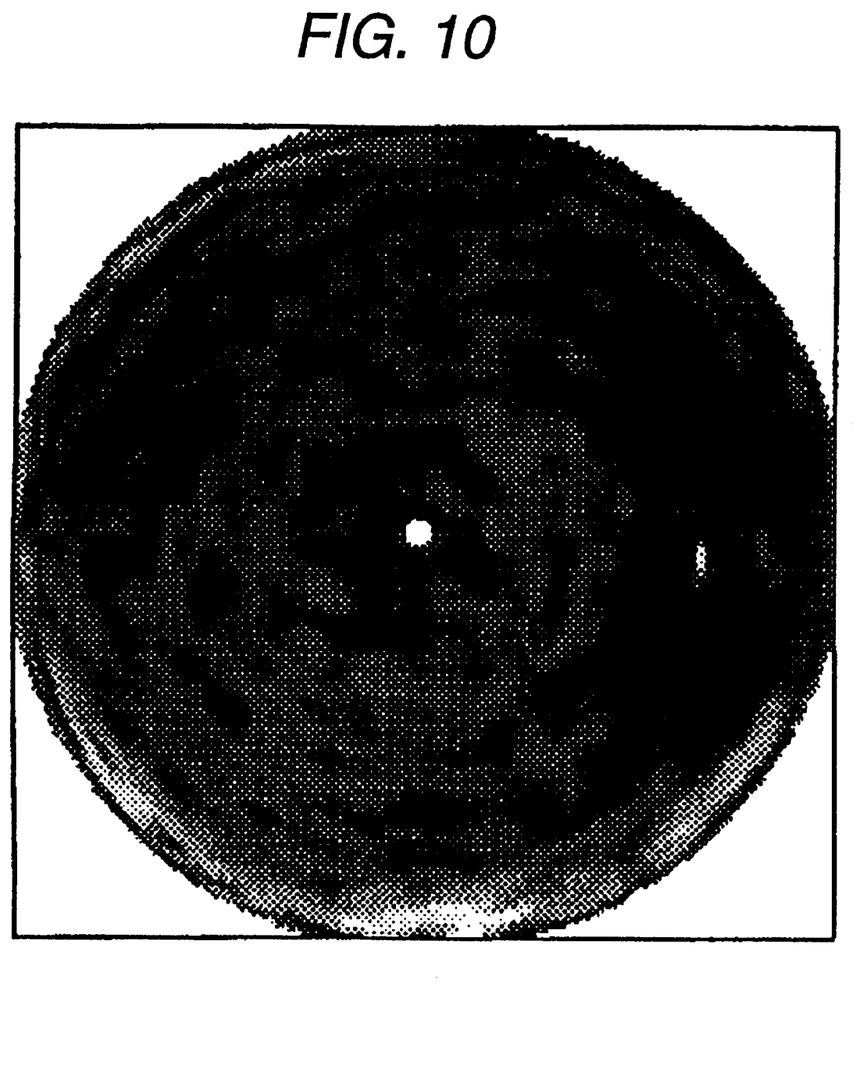
FIG. 10 is an example of a display of haze in a silicon wafer expressed by a wafer planar distribution.

FIG. 10 is a conventional example of a wafer planar distribution of hazes in a silicon wafer. The haze is for evaluating unevenness of surface, which depends on surface finishing, and is effective for evaluating surface working process in a wafer manufacturer.

In the planar distribution shown in FIG. 10, scattering intensity due to haze is toned by displaying high intensity portions by white and low intensity portions by black. It is possible to some degree to judge the magnitude or the density of haze on the surface by this display, but it is impossible to objectively judge that the haze affects the electric characteristic or the insulation withstanding voltage of LSI or ULSI elements and whether or not the haze is at a level to perform feedback to the wafer working process.

Figure 11:
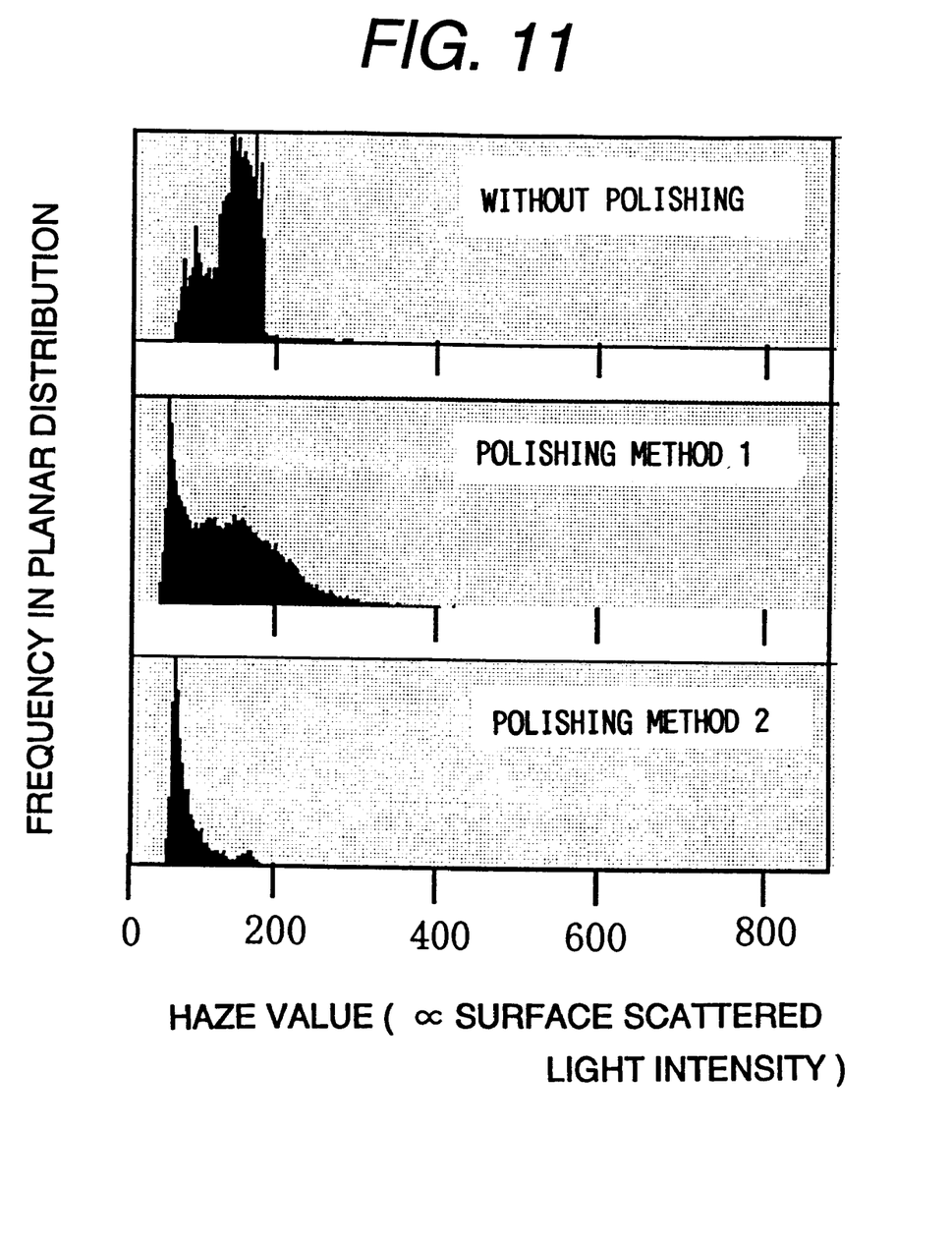
FIG. 11 is an example of a display expressing frequency distribution for each scattered light intensity by haze.

FIG. 11 is displays of frequency distribution for each scattered light intensity due to haze. The scattered light intensity due to haze relates to the electric characteristic or the insulation withstanding voltage of LSI or ULSI elements. Therefore, by defining connection with the frequency distribution display of the intensity, it is possible to perform feedback to the wafer working process or the polish working process.

Further, when haze is high, an alternative current component due to the haze becomes large (in proportion to a square root of the haze). When haze is larger than a threshold value of defect detecting mode, the haze is erroneously detected as a defect. Therefore, by viewing the frequency distribution display of the intensity, it is possible to easily evaluate the reliability of a detected defect inside a wafer. By expressing haze values in a histogram, it is possible to purely detect as a frequency of uneven regions on the sample surface.

In the example of FIG. 11, since number of haze signals is larger in polishing method 1 than in the case of without polishing, it can be understood at a glance that the polishing is bad. On the other hand, since number of haze signals in polishing method 2 is clearly decreased, it can be proved that the polishing result is good.

The method of measuring the haze in the apparatus of this embodiment is different from the defect detection in detecting method.

In the defect detection mode, as described previously, when a scattered light signal from a defect exceeds a preset threshold value, the signal intensity and the (R, θ) coordinates are acquired.

On the other hand, in the haze measurement mode, scattered light intensity of 532 nm light and the (R, θ) coordinates are acquired with a certain time interval or a certain angle interval of the rotating stage irrespective of presence and absence of defect. In the case of the apparatus of the present embodiment, the data is acquired every certain time interval or the data is acquired every certain preset angle while the sample wafer is being spirally scanned at a constant linear velocity. The data acquired in such a manner is spread over the whole wafer surface differently from the defect distribution diagram. A haze map is formed by smoothly interpolate between scattered light intensities in the points.

Figure 12:
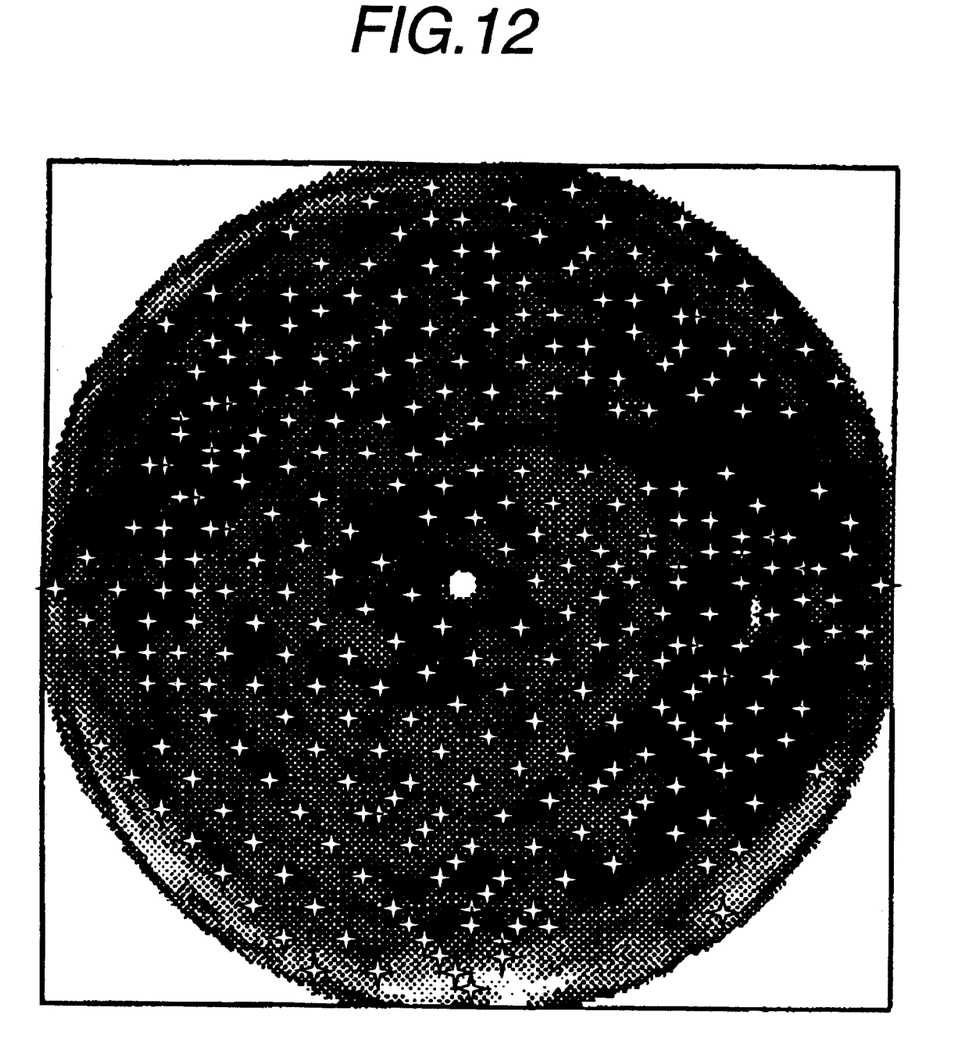
FIG. 12 is an example of a display expressed by superposing a distribution of defects of a measured result on a planer distribution of scattered light intensities by haze.

FIG. 12 is a display expressed by superposing a distribution of defects of a measured result on a planer distribution of scattered light intensities by haze. In the figure, the defect results are expressed by cross marks. By displaying the haze distribution and the defect distribution together, it is possible to judge whether a defect is a defect due to haze or not.

Figure 13:
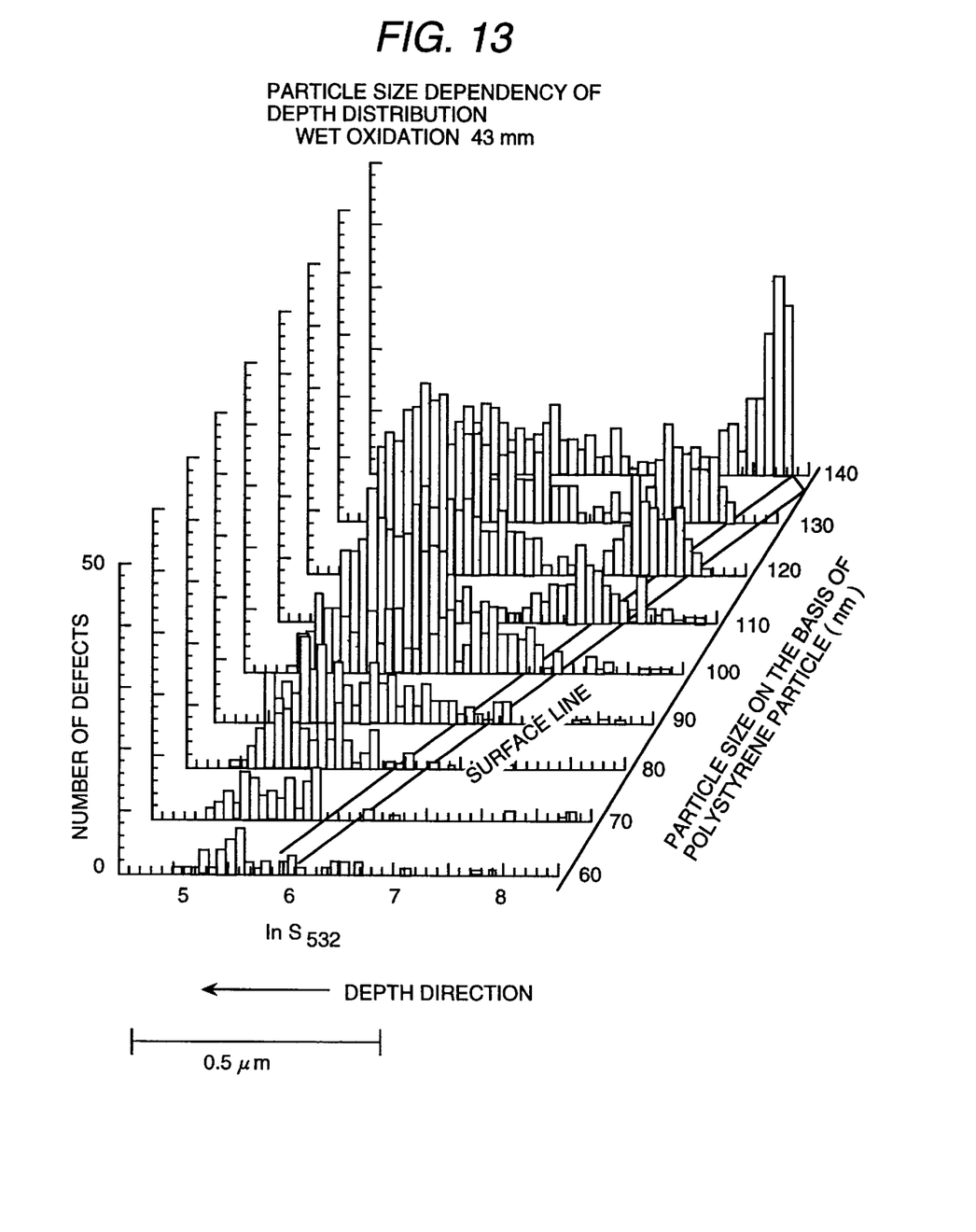
FIG. 13 is a graph showing a particle size dependency of depth distribution.

FIG. 13 is a graph showing an example of distribution display based on depth, size (particle size) and number of defects obtained by the apparatus of the present embodiment. In this example of display, the X-axis is depth of defects (ln(S532)) to the surface line extending in slant in the figure, the Y-axis is size of detects (particle size on the basis of polystyrene particle), and the Z-axis is number of defects. Therein, the Y-axis is grouped by a predetermined particle size interval unit.

This graph shows a defect inspection result by the apparatus of the present embodiment using a silicon wafer obtained by performing wet oxidizing treatment to form an oxide film of 43 nm and then removing the oxide film.

By such a display, it becomes easy to judge whether the defects are defect (COP) formed on the wafer surface by the oxidizing treatment or crystal defects inside the wafer.

COP is increased in number by forming the oxide film, and is a defect having a relatively large particle size. A graph taking particle size in the abscissa and number of defects in the ordinate is disclosed in the proceeding of 1996 International Conference on Solid Stare Devices and Materials, pages 151–153, but the COP cannot be selectively checked by the display of this type. The reason is that it is impossible to check whether a defect is a COP or a crystal defect because COPs and in-crystal defects having an equivalent particle size are mixed. Further, a graph taking depth in the abscissa and number of defects in the ordinate is disclosed in the above proceeding, but it is difficult to judge whether a defect existing on the sample surface (sample depth is near 0) is a COP or not.

The display mode of the present embodiment is for solving the above-mentioned problem, and it is possible to easily check generation of distinguishable defect by specifying two elements of particle size and depth. In the example of display shown in FIG. 13, it can be understood that a swelling portion of the distribution in upper right in the figure indicates COPs, and a swelling portion of the distribution in upper left in the figure indicates crystal defects existing inside the wafer.

Instead of the three-dimensional display shown in FIG. 13, a two-dimensional graph having coordinates of particle size and depth may be useful. In this case, number of defects is riot grouped by a predetermined particle size interval unit, but a display of scatter diagram type is employed based on particle size data possessed by each defect. By doing so, a defect concentrating position is visually detectable. That is, taking the sample of FIG. 13 as an example, a scatter diagram having defect concentrating portions in a sallow portion and a deep portion in a large particle size region is obtained. It is possible to judge the trend of generating the COP and the crystal defect by the degree of the concentration.

The apparatus of this embodiment relates to an apparatus capable of detecting depth of defect and size (particle size) of defects, and generation of defects such as COP can be easily detected by displaying a defect distribution having at least coordinate axes of depth and particle size.

As described above, according to the present invention, since defect affecting the device characteristics can be quantitatively evaluated and the defect causes can be objectively identified, it is possible to easily perform appropriate feedback to the wafer manufacturing processes.

What is claimed is:

1. A defect inspection apparatus for detecting defects existing on a surface of a sample and/or inside the sample based on light information from the sample obtained by irradiating a light beam onto the sample, which comprises:

a detecting means for detecting, at a location where a defect exists, corresponding to a position of the said light beam, depth information and size information of said defect based on said light information; and a display apparatus for displaying a distribution of said defects on a graph having as coordinate axes a depth of said defect and a size of said defect, based on the depth information and the size information obtained by said detecting means.

2. A defect inspection apparatus for detecting defects as defined in claim 1, wherein said display apparatus displays said distribution and said size of said defects based on positional information obtained by said detecting means.

3. A defect inspection apparatus according to claim 1, wherein, said detecting means comprises a means for obtaining information about a number of said defects corresponding to positions of the said light beam by counting said defects; and said display apparatus comprises means for displaying said depth and said size of defects together with a graph having a coordinate axis indicating the number of defects, and displaying said number of defects versus said depth of defects for each predetermined unit of defect size on said graph based on said information on depth, size and number of defects.

* * * * *